United States Patent
Katschnig et al.

[19]

[11] Patent Number: 5,879,643
[45] Date of Patent: Mar. 9, 1999

[54] MICROWAVE APPARATUS FOR HEATING, DISINFECTING AND STERILIZING MATERIALS

[75] Inventors: Helmut Katschnig, Burggasse 108, 8750 Judenburg; Wolfgang Stegmüller, St. Peter/Judenburg; Ernst Gruber, Judenburg, all of Austria

[73] Assignee: Helmut Katschnig, Judenburg, Austria

[21] Appl. No.: 681,091

[22] Filed: Jul. 22, 1996

[30] Foreign Application Priority Data

Jul. 24, 1995 [AT] Austria ................................ 1258/95

[51] Int. Cl.⁶ .......................... A61L 2/00; G08B 21/00; B01B 0/00; G05D 0/00
[52] U.S. Cl. ................. 422/307; 422/107; 422/302; 422/21; 340/603; 250/574; 60/618
[58] Field of Search ...................... 422/107, 307, 422/302, 21; 356/439; 340/603, 628; 250/574; 60/618

[56] References Cited

U.S. PATENT DOCUMENTS

| | | | |
|---|---|---|---|
| 3,945,210 | 3/1976 | Chapin | 60/618 |
| 4,608,556 | 8/1986 | Cole | 340/628 |
| 4,931,774 | 6/1990 | Bachman | 340/603 |
| 5,220,179 | 6/1993 | Gagea | 250/574 |
| 5,363,199 | 11/1994 | Victor et al. | 356/439 |
| 5,403,564 | 4/1995 | Katschnig et al. | 422/307 |
| 5,407,641 | 4/1995 | Katschnig et al. | 422/107 |
| 5,410,299 | 4/1995 | Hard | 340/628 |

*Primary Examiner*—Ponnathapura Achutamurthy
*Assistant Examiner*—Hankyel T. Park
*Attorney, Agent, or Firm*—Henry M. Feiereisen

[57] ABSTRACT

Apparatus for heating, disinfecting and sterilizing materials through exposure to microwave radiation; includes a treatment chamber which houses a container filled with material to be treated. An injector is in fluid communication with the container for introducing a liquid to the material and includes a dome which is tightly placed on top of the container, and a nozzle which is secured interiorly of the dome and projects through an opening of the container for injecting liquid into the treatment chamber. An exhaust conduit further projects into the dome for discharge of exhaust fluid from within the container directly to an area outside of the treatment chamber.

15 Claims, 1 Drawing Sheet

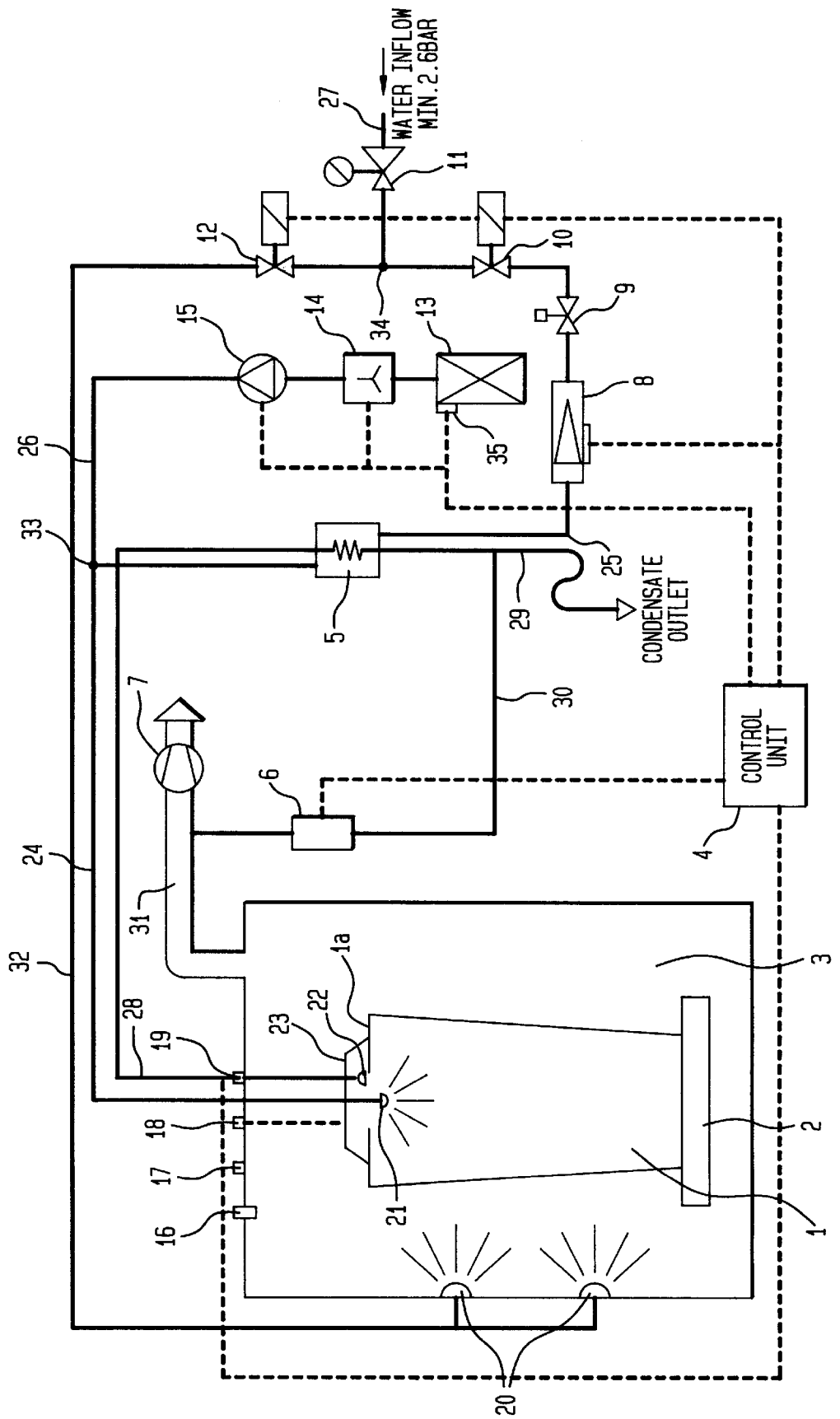

MICROWAVE APPARATUS FOR HEATING, DISINFECTING AND STERILIZING MATERIALS

BACKGROUND OF THE INVENTION

The present invention refers to an apparatus for heating, disinfecting and sterilizing materials by exposing the material to microwave radiation in a treatment chamber in which a container receiving the material is placed.

A microwave apparatus of this type is typically used for heating, disinfecting and sterilizing various materials such as refuse from hospitals, kitchen garbage etc., and is known for example from U.S. Pat. No. 5,246,674. The microwave apparatus includes a container which is placed in a treatment chamber and is closed by a lid formed with a central opening for receiving an injector that introduces liquid, for example water, optionally mixed with additives, to the material in the container. The injector is further equipped with a temperature sensor and a pressure sensor. Steam generated in the container escapes into the treatment chamber and is then discharged to the outside. The entry of exhaust into the treatment chamber is disadvantageous because the microwave apparatus is unable to react instantly to a presence of vapor and/or smoke accumulating in the treatment chamber before being discharged.

SUMMARY OF THE INVENTION

It is an object of the present invention to provide an improved microwave apparatus obviating the afore-stated drawbacks.

In particular, it is an object of the present invention to provide an improved microwave apparatus that rapidly responds to the presence of smoke and/or steam by suitably adjusting the magnetrons that produce the output of microwave radiation.

These objects and others which will become apparent hereinafter are attained in accordance with the present invention by providing an injector which is comprised of a dome placed directly onto the container lid, and an injector nozzle which is secured interiorly to the dome and projects into the opening of the container for introducing liquid, and by incorporating an exhaust conduit that projects into the dome for discharge of exhaust gas and exhaust steam from the container directly outside of the treatment chamber.

Through placement of a dome upon the container and provision of a separate exhaust conduit that directly connects the interior of the container with an area outside of the treatment chamber, smoke and steam generated during microwave treatment is prevented from exiting the container into the treatment chamber so that an immediate response to possible smoke formation or other safety hazards is effected by the safety devices despite their disposition outside of the treatment chamber.

Preferably, the exhaust conduit is monitored by a temperature sensor which rapidly responds to the concentrated discharge of exhausts through the dome and the exhaust conduit and provides a measurement of the actual temperature. Further monitoring the exhaust conduit is a smoke detector that rapidly determines the presence of smoke and/or vapor in the exhaust conduit as a result of the concentrated discharge of the exhaust gas and exhaust steam. Thus, the overall safety aspect of the microwave apparatus is considerably enhanced.

According to another feature of the present invention, a condenser is positioned upstream of the smoke detector so that the necessity to incorporate complicated differentiation devices that distinguish between smoke and steam is eliminated. The output line of the condenser leads to an exhaust gas conduit which extends out of the treatment chamber and has incorporated therein an exhaust fan, with the output line preferably entering the exhaust gas conduit upstream of the exhaust fan to ensure that all exhaust steam formed during microwave radiation exits together the apparatus. The provision of the exhaust fan further ensures that formation of condensate within the treatment chamber as a result of released steam is prevented.

Suitably, fresh water is injected into the interior of the treatment chamber via extinguisher nozzles which are disposed at least on one wall of the treatment chamber to immediately suppress any possibility of fire development. In order to improve the overall energy consumption of the system and to render the process less time consuming through decrease of the heating time for water that is introduced into the container, the fresh water is preheated by conducting the fresh water through the condenser before injection into the treatment chamber. Thus, fresh water is preheated and the condenser is cooled down so that the overall treatment cycle is substantially shortened.

According to another feature of the present invention, the treatment chamber is provided with a vertical drop detector for sensing the presence of a container within the treatment chamber by monitoring the distance the dome is lowered for placement on the container. The vertical drop detector is connected to an alarm and safety mechanism which is triggered when the detector determines that no container is actually placed within the treatment chamber or that the container itself has collapsed as a result of a softening of the container due to excess temperature.

Suitably, the temperature sensor, the smoke detector and the vertical drop detector are operatively connected to a central control unit which processes the information inputted to thereby adjust the energy supply to the microwave generators and/or the amount of liquid introduced into the treatment chamber through the injector. Thus, the presence of excess temperatures or the detection of a melting or collapse of the container results in an automatic shutdown of the apparatus and upon detection of smoke within the container results in an injection of water into the container to suppress any fire development.

The control unit may be further connected to a thermoswitch located in the treatment chamber and/or with a light sensor or infrared sensor that is also arranged in the treatment chamber, and optionally, to the extinguisher nozzles which project into the treatment chamber and inject water into the treatment chamber, when the thermoswitch registers an excess temperature or the light sensor registers a fire, to prevent development of progressive fire and at the same time effect a cooling of the container to maintain its stability.

With a microwave apparatus according to the present invention, the water consumption as well as the consumption of odor neutralizers can be optimized. Moreover, the fluid-tight sealing of the container by the dome minimizes presence of bad odor, and the energy consumption is reduced through preheating water before being injected into the treatment chamber while at the same time cooling generated steam and substantially minimizing a risk of fire. Thus, the safety aspect of the microwave apparatus according to the present invention is considerably enhanced and the overall cost efficiency of the process is significantly improved.

BRIEF DESCRIPTION OF THE DRAWING

The above and other objects, features and advantages of the present invention will now be described in more detail with reference to the accompanying drawing in which the sole FIGURE illustrates a simplified, schematic illustration of a microwave apparatus in accordance with the present invention for treating material in a container.

DETAILED DESCRIPTION OF A PREFERRED EMBODIMENT

Turning now to the sole FIGURE, there is shown a simplified, schematic illustration of a microwave apparatus in accordance with the present invention for treating material in a container 1 which is placed on a turntable 2 of a treatment chamber 3. The treatment chamber 3 is part of a microwave device that radiates microwave energy generated by a plurality of magnetrons in a manner known per se, to thereby prevent the presence of dead or cold areas within the treatment chamber 3. The container 1 is closed by a lid 1a which is formed with a central opening 22. A dome 23 is placed onto the lid 1a in a fluidtight manner to seal the opening 22 from the outside. The dome 23 is rotatably secured inside the treatment chamber in a manner not shown in detail to a mounting, e.g. via a slide ring.

Projecting through the dome 23 into the opening 22 is a conduit 24 which terminates in an injector nozzle 21 for introduction of liquid, e.g. water, into the container 1 and to the material being treated. The nozzle distant end of the conduit 24 leads via a T connector 33 to a heat exchanger in form of a condenser 5. Joined to the T connector 33 is a further conduit 26 for optional supply of deodorant from a reservoir 13 by means of a pump 15, e.g. a hose pump. A flowmeter 14 is disposed in the conduit 26 to measure the flow rate and to enable admixture of a controlled dose of deodorant to water conducted in the conduit 24. Suitably, the reservoir 13 is equipped with a level indicator 35 to monitor the content of deodorant within the reservoir 13.

Liquid, e.g. fresh water, supplied to the injector nozzle 21 is conducted from the condenser 5 which receives fresh water from a water reservoir (not shown) via a conduit 25. The liquid enters the system at a pressure of at least 2.5 bar at an amount which is controlled by a pressure reducing valve 11 positioned in a water conduit 27 that leads from the water reservoir to a T connector 34 for connection of the conduit 25. The amount of liquid actually supplied to the condenser 5 is controlled by a solenoid valve 10 via a flowmeter 8 and a needle valve 9 which are disposed in the conduit 25. The T connector 34 further communicates with a conduit 32 which conducts fresh water to extinguisher nozzles 20 that are arranged on one wall of the treatment chamber 3 to inject fresh water into the treatment chamber 3 in case of need. The flow of fresh water is regulated by a solenoid valve 12 which is disposed in the conduit 32.

As indicated by broken lines, the solenoid valves 10, 12, the flowmeter 8, the level indicator 35 of the reservoir 13, the flowmeter 14 and the hose pump 15 for the deodorant are operatively connected to a central control unit 4 which controls the overall process with regard to the water amount and energy supply to the magnetrons.

Projecting into the dome 23 is further an exhaust conduit 28 which is led through the condenser 5. Thus, heat contained in the exhaust gas or exhaust steam is used to raise the temperature of fresh water supplied thereto and used for introduction into the container 1 via conduit 24 and injector nozzle 21. Liquid condensing from the steam is drained via the condensate conduit 29, while the dried, gaseous phase is conducted via a conduit 30 to a smoke detector 6 for monitoring any smoke development in the dry exhaust gas and transmitting signals commensurate with the detection operation to the control unit 4, as indicated by broken line, for further processing. Outgoing air exiting the smoke detector 6 is conducted to the exhaust gas conduit 31 which extends out from the treatment chamber 3. An exhaust fan 7 is positioned in the exhaust gas conduit 31, whereby the entrance of dry outgoing air from the smoke detector 6 enters the exhaust gas conduit 31 at a location upstream of the exhaust fan 7 to ensure that all exhausts are drawn to the outside.

The treatment chamber 3 is further provided with an infrared or light sensor 16 which is also connected to the control unit 4, as indicated by broken line. Additional measuring devices include a thermoswitch 17 which is activated at a certain temperature level, and a vertical drop detector 18 by which the distance of the dome 23 being lowered for placement on the container 1 is measured. Also the thermoswitch 17 and the vertical drop detector 23 are connected to the control unit 4, as indicated by broken lines. Thus, the solenoid valve 12 is activated by the control unit 4 to supply fresh water to the extinguisher nozzles 20 for injection into the treatment chamber 3 when the thermoswitch 17 or the infrared or light sensor 16 signal to the control unit 4 the presence of a fire within the treatment chamber 3.

Disposed in the exhaust conduit 28 is a temperature sensor 19 which monitors the temperature of exhaust exiting the container 1, and is suitably connected to the control unit 4, as indicated by broken line.

The microwave apparatus according to the invention thus provides an automatic system to effectively moisten the material being treated and to monitor the process. In particular, two problems relating to the use of microwave devices for treatment of materials, such as heterogeneous refuse material, through e.g. pressureless thermal disinfection, are solved, namely, on the one hand effecting an even moistening of the material, while still preventing an excessive moistening in order to minimize the energy consumption, and on the other hand eliminating any risk of fire as a result of sufficient moistening.

Typically, before being exposed to microwave radiation, the refuse material is moistened either manually or automatically by adding an appropriate amount of water. Preferably, the addition of water is carried out in a fully automatic manner, e.g. in a manner as described in U.S. Pat. No. 5,246,674, by providing the turntable 2 in form of a scale plate which weighs the container 1 and calculates on the basis of the determined weight through application of a particular algorithm the required amount of water. This conventional microwave apparatus, however, does not take into consideration the use of waterproof trash bags for accommodating the dry refuse materials so that despite automatic water supply a moistening of the material inside the sealed trash bags will not be effected. Thus, the heating action may cause the refuse to ignite and result in fires within the container when not providing the trash bag with means that form an opening when being excessively heated.

In accordance with the present invention, the use of biological trash bags is thus preferred which dissolve at a temperature above 80° C. so that a generally even moistening action of the entire refuse material inside the container 1 during the treatment cycle is effected. Possible charging errors that may result in fire are recognized in time by the infrared sensors 16 and the thermoswitch 17 as well as by the temperature sensor 19 so as to cause a shutdown of the microwave generators and introduction of water either via the injector nozzle 21 or extinguisher nozzles 20.

At operation, the container 1 with the refuse is placed in the treatment chamber 3 upon the turntable 2, whereby the amount of water injected by nozzle 21 is calculated on the basis of the weight of the container 1, in a manner as described in U.S. Pat. No. 5,246,674. After closing the access door to the treatment chamber 3, the elastic dome 23 is automatically lowered onto the container 1, whereby the vertical drop detector 18, through monitoring the distance that the dome 23 is lowered, determines whether indeed a container 1 is positioned within the treatment chamber 3. If the detector 18 registers that the dome 23 is lowered excessively, the microwave apparatus cannot be activated even though the access door is closed. The dome 23 is placed in fluidtight manner on the lid 1a of the container 1, with the injection nozzle 21 that projects into the opening 22 injecting liquid into the container 1 at an amount that is calculated in a manner described above. Persons skilled in the art will understand that the opening 22 may also be sealed by a membrane which is then pierced by the injection nozzle 21 when the dome 23 is placed on the lid 1a of the container 1. A rotation of the container 1 as imparted by the turntable 2 is compensated by the rotatable support of the dome 23 to the lowering mechanism which is thus not turned despite the rotation of the container 1.

The program cycle of the control unit 4 starts with operation of the turntable 2 and, after calculation of the right amount, injection of liquid into the container 1 through the injection nozzle 21 via operation of the solenoid valve 10, needle valve 9 and the flowmeter 8. Optionally, the liquid may be mixed with an amount of deodorant that is supplied from the reservoir 13 and conducted through the flowmeter 14 and the hose pump 15 via the conduit 26.

After activating the microwave generators, the liquid within the refuse is brought to boiling temperature, with the outgoing air from the container 1 containing steam at a temperature that is measured by the temperature sensor 19 in the exhaust conduit 28. When reaching the boiling phase, the microwave device automatically shuts down to a predetermined retention time for the disinfection cycle. The heating time ranging from start of activation of the magnetrons to reaching of the boiling temperature within the refuse or the given temperature in the outgoing air can vary and depends from the liquid amount within the container 1. Thus, regardless of the refuse composition and the liquid amount in the container 1, the intended disinfection time commences only after reaching the steam temperature in the entire refuse material so that a secure disinfection action is ensured even with heterogeneous refuse material and without knowledge of the actual material content.

The exhaust gas or exhaust steam exiting the container 1 through the dome 23 via the conduit 28 is conducted to the condenser 5 through which fresh water is guided in counterflow via the conduit 24 for moistening the material being treated. The condenser 5 effects a heating of the fresh water introduced during the subsequent disinfection cycle so that the second disinfection cycle can be operated at reduced heating time as a result of the preheated water. Exhaust exiting the container 1 is aspirated after passage through the condenser 5 by the exhaust fan 7 while passing through the smoke detector 6 to enable an early recognition of possible smoldering fire within the container 1. Immediately after signaling a fire within the container 1, the control unit 4 automatically shuts down the microwave apparatus and activates the injection of water into container 1. The exhaust fan 7 not only effects a discharge of the exhaust from the container 1 but also a ventilation of the treatment chamber 3 to avoid condensation of water within the treatment chamber 3.

A possible light development within the treatment chamber 3 as a result of ignited refuse is registered by the light sensor or infrared sensor 16 and signaled to the control unit 4 which shuts down the microwave apparatus and, if necessary, activates the extinguisher nozzles 20. A shutdown of the microwave apparatus can also be effected by the thermoswitch 17 which operates as overheat switch which is activated at registration of a certain excess temperature and positioned at the outer wall of the treatment chamber 3. Upon registration of an excess temperature, the thermoswitch 17 signals to the control unit 4 to activate the injection of water through the extinguisher nozzles 20.

The vertical drop detector 18 is equipped with a particular altimeter to detect whether a container 1 is placed within the treatment chamber 3 or whether the container 1 has collapsed due to melting as a result of excess temperatures. Also in the latter case, i.e. at sinking container, the microwave apparatus is shutdown automatically by the control unit 4 and liquid is injected into the treatment chamber 3 via the nozzle 21 as well as the extinguisher nozzles 20 to prevent a further softening of the container 1.

Through the entire treatment cycle, the container 1 is continuously turned by the turntable 2, with the opening 22 being hermetically sealed by the elastic dome 23 despite the rotation of the container 1.

It will be understood by persons skilled in the art that the microwave apparatus according to the present invention can also be operated at excess pressure or underpressure.

While the invention has been illustrated and described as embodied in a microwave apparatus for heating, disinfecting and sterilizing materials, it is not intended to be limited to the details shown since various modifications and structural changes may be made without departing in any way from the spirit of the present invention.

What is claimed as new and desired to be protected by Letters Patent is set forth in the appended claims:

We claim:

1. Apparatus for heating, disinfecting and sterilizing materials through exposure to microwave radiation; comprising:

a treatment chamber for housing a container filled with material to be treated;

microwave radiation means for exposing the treatment chamber to microwave radiation;

a dome rotatably secured within the treatment chamber and destined to be lowered for tight placement onto the container after the treatment chamber is closed;

an injector in fluid communication with the container for introducing a liquid to the material, said injector including a nozzle secured interiorly of the dome and projecting through an opening of the container for injecting liquid; and an exhaust conduit projecting into the dome for discharge of exhaust from the container to an area outside the treatment.

2. The apparatus of claim 1, and further comprising a control unit operatively connected to the microwave radiation means for controlling an energy supply and thereby the microwave radiation in the treatment chamber, and to the injector for controlling the amount of liquid introduced into the treatment chamber.

3. The apparatus of claim 1, and further comprising a temperature sensor positioned in the exhaust conduit for monitoring the temperature of exhaust in the exhaust conduit.

4. The apparatus of claim 2, and further comprising a temperature sensor providing a signal commensurate with the temperature of exhaust in the exhaust conduit, said temperature sensor being operatively connected to the control unit for input of the signal.

5. The apparatus of claim 1, and further comprising a smoke detector operatively connected to the exhaust conduit and positioned in an outlet line leading from the exhaust conduit to the smoke detector for monitoring presence of smoke and/or vapor in the exhaust conduit.

6. The apparatus of claim 2, and further comprising a smoke detector providing a signal commensurate with the presence of smoke and/or vapor in the exhaust conduit, said smoke detector being operatively connected to the control unit for input of the signal.

7. The apparatus of claim 5, and further comprising a condenser positioned upstream of the smoke and/or vapor detector in the outlet line and cooled by liquid introduced into the container.

8. The apparatus of claim 7 wherein the outlet line terminates in an exhaust gas conduit extending outwards from the treatment chamber.

9. The apparatus of claim 8, and further comprising an exhaust fan positioned in the exhaust gas conduit, said outlet line communicating with the exhaust gas conduit at a location before the exhaust fan.

10. The apparatus of claim 1, and further comprising a vertical drop detector for monitoring a distance by which the dome is lowered in direction of the container.

11. The apparatus of claim 2, and further comprising a vertical drop detector forming a signal commensurate with a distance by which the dome is lowered in direction of the container, said vertical drop detector being operatively connected to the control unit for input of the signal.

12. The apparatus of claim 2, and further comprising a thermoswitch positioned in the treatment chamber and operatively connected to the control unit.

13. The apparatus of claim 2, and further comprising a light sensor positioned in the treatment chamber and operatively connected to the control unit.

14. The apparatus of claim 2, and further comprising extinguisher nozzles projecting into the treatment chamber for injection of water into the treatment chamber, said extinguisher nozzles being operatively connected to the control unit.

15. The apparatus of claim 1 wherein liquid injected by the nozzle and exhaust discharged through the exhaust conduit are guided in counterflow direction to enable a heat exchange between liquid and exhaust.

\* \* \* \* \*